(12) United States Patent
Greim

(10) Patent No.: US 9,791,527 B2
(45) Date of Patent: Oct. 17, 2017

(54) EXTENDED DETUNING IN LOCAL COILS

(71) Applicant: Helmut Greim, Adelsdorf (DE)

(72) Inventor: Helmut Greim, Adelsdorf (DE)

(73) Assignee: Siemens Aktiengesellschaft, München (DE)

( * ) Notice: Subject to any disclaimer, the term of this patent is extended or adjusted under 35 U.S.C. 154(b) by 596 days.

(21) Appl. No.: 14/319,126

(22) Filed: Jun. 30, 2014

(65) Prior Publication Data

US 2015/0015262 A1 Jan. 15, 2015

(30) Foreign Application Priority Data

Jul. 9, 2013 (DE) .................. 10 2013 213 377

(51) Int. Cl.
*G01V 3/00* (2006.01)
*G01R 33/385* (2006.01)
*G01R 33/36* (2006.01)
*A61B 5/055* (2006.01)
*G01R 33/341* (2006.01)

(52) U.S. Cl.
CPC ....... *G01R 33/385* (2013.01); *G01R 33/3642* (2013.01); *A61B 5/055* (2013.01); *G01R 33/341* (2013.01)

(58) Field of Classification Search
CPC .................................................. G01R 33/385
USPC ................................. 324/322, 318
See application file for complete search history.

(56) References Cited

U.S. PATENT DOCUMENTS

| 5,202,634 | A | * | 4/1993 | Potthast | ............ | G01R 33/3628 |
| | | | | | | 324/318 |
| 5,221,901 | A | * | 6/1993 | Decke | ................ | G01R 33/3628 |
| | | | | | | 324/318 |
| 5,621,323 | A | | 4/1997 | Larsen | | |
| 5,646,530 | A | | 7/1997 | Strenk et al. | | |
| 6,414,488 | B1 | * | 7/2002 | Chmielewski | ..... | G01R 33/3657 |
| | | | | | | 324/311 |
| 7,999,548 | B1 | * | 8/2011 | Brown | .................... | A61B 5/055 |
| | | | | | | 324/307 |
| 2005/0127914 | A1 | | 6/2005 | Eberler et al. | | |

(Continued)

FOREIGN PATENT DOCUMENTS

| CN | 1534305 A | 10/2004 |
| CN | 101539614 A | 9/2009 |

(Continued)

OTHER PUBLICATIONS

Chinese office Action for related Chinese Application No. 2014 103 191 44.3 dated Sep. 2, 2016 with English Translation.

(Continued)

*Primary Examiner* — Louis Arana
(74) *Attorney, Agent, or Firm* — Lempia Summerfield Katz LLC

(57) ABSTRACT

A local coil for an MRI imaging system includes an antenna containing a first detuning circuit and a second detuning circuit, and a connection connected to the antenna between a first connection point on the antenna and a second connection point on the antenna. The connection is configured to be short-circuited by at least one diode. The first connection point and the second connection point are situated spatially between a first partial region and a second partial region of the antenna.

20 Claims, 7 Drawing Sheets

(56) References Cited

U.S. PATENT DOCUMENTS

2009/0237081 A1    9/2009  Biber et al.

FOREIGN PATENT DOCUMENTS

DE    4309370    9/1994
DE    10314215   10/2004

OTHER PUBLICATIONS

German Office Action dated Dec. 4, 2013 in corresponding German Patent Application No. DE 10 2013 213 377.4 with English translation.

* cited by examiner

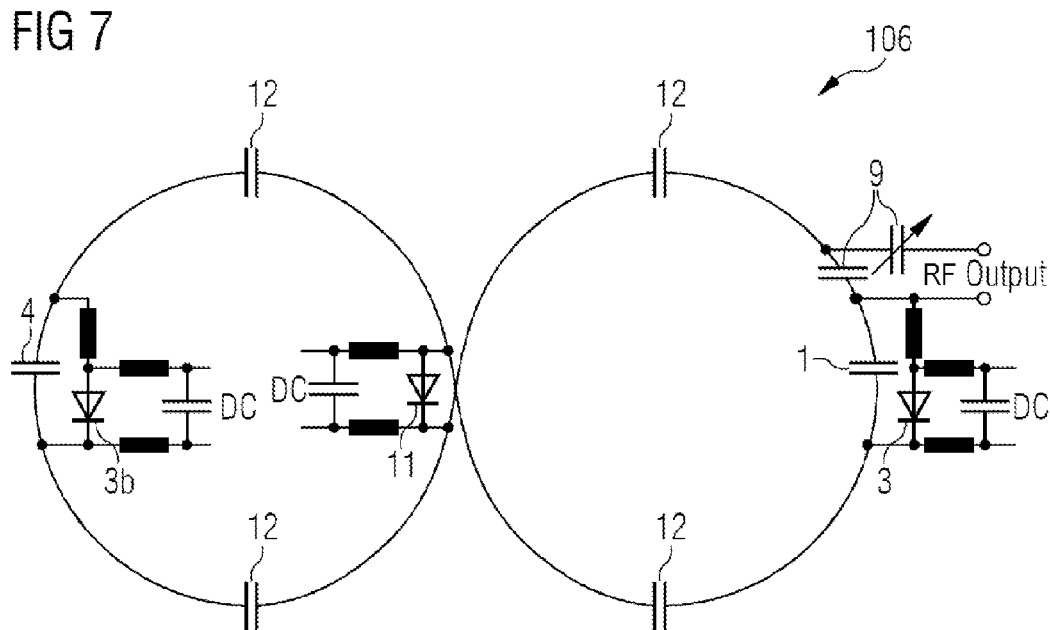

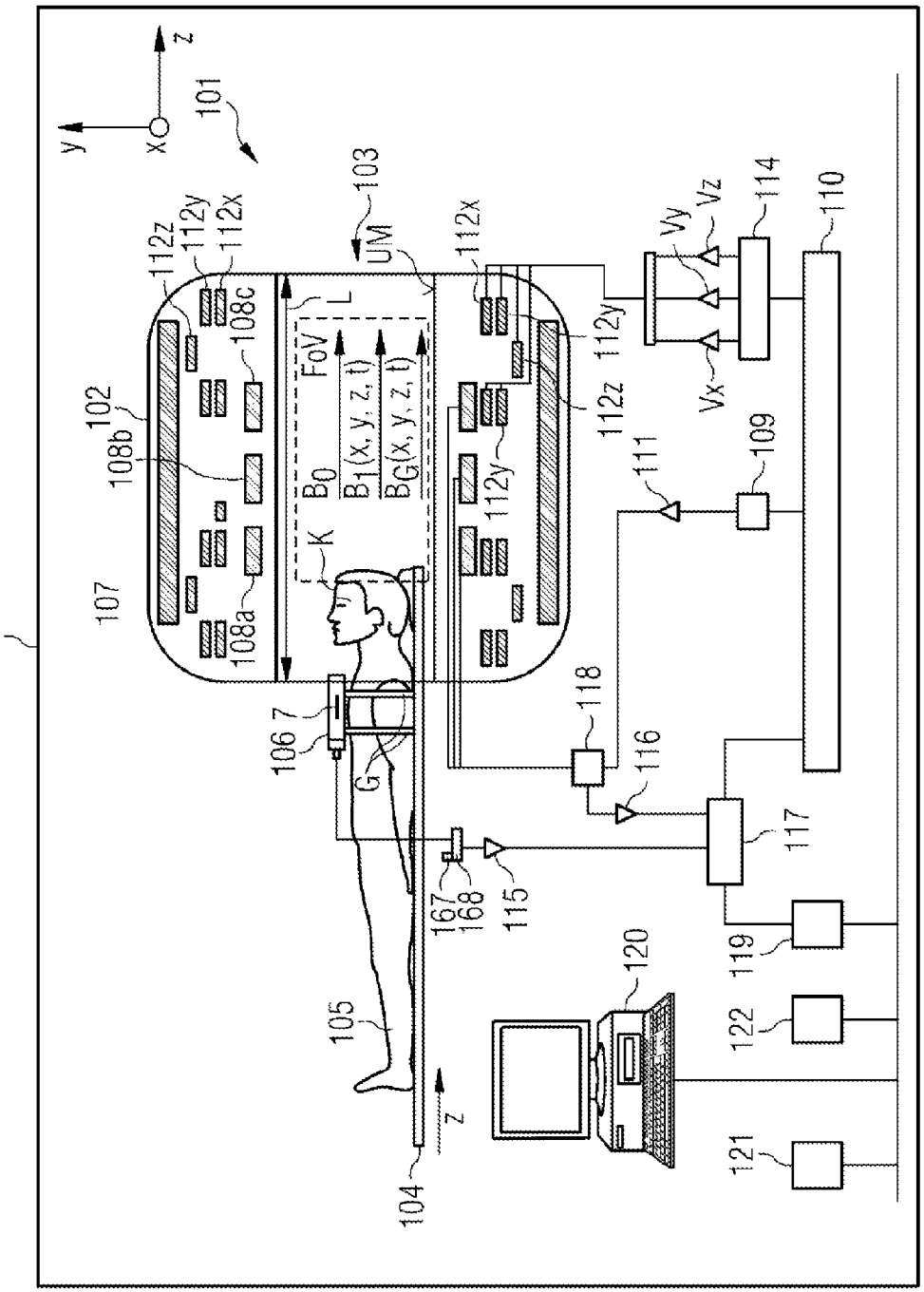

EXTENDED DETUNING IN LOCAL COILS

RELATED APPLICATIONS

This application claims the benefit of German Patent Application No. DE 102013213377.4, filed Jul. 9, 2013. The entire contents of the priority document are hereby incorporated herein by reference.

TECHNICAL FIELD

The present teachings relate generally to local coils.

BACKGROUND

Magnetic resonance imaging (MRI) apparatuses for examining objects or patients by magnetic resonance imaging are described, for example, in DE 10314215 B4.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a local coil is provided.

BRIEF DESCRIPTION OF THE DRAWINGS

FIG. 7 shows an example of a "figure-eight" loop antenna of a local coil with two detuning circuits and two additional diodes in the center.

FIG. 8 shows an example of an MRI system.

DETAILED DESCRIPTION

Figure 1:
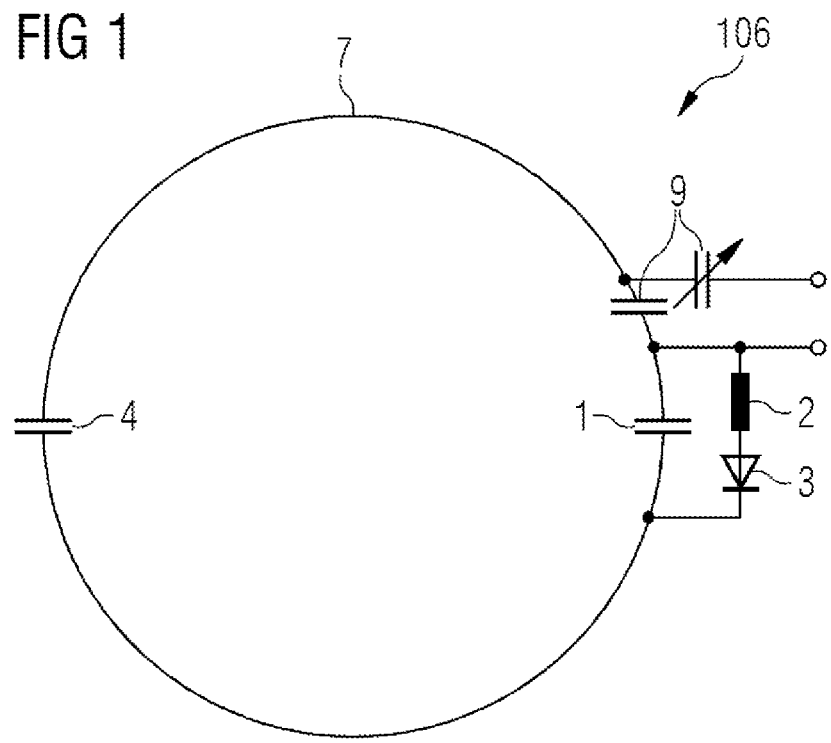
FIG. 1 shows an example of a circular loop antenna of a local coil with one detuning circuit.

FIG. 8 shows inter alia a magnetic resonance imaging (MRI) apparatus 101 in a shielded area or Faraday cage F. The apparatus 101 includes a whole body coil 102 with a tubular space 103. A patient couch 104 with a body 105 (e.g., of an examination object, such as a patient), with or without a local coil arrangement 106, may be moved in the direction of the arrow z in order to generate recordings of the patient 105 by an imaging method. The local coil arrangement 106 is arranged on the patient and may be used to generate in a local region of the MRI (also called a field of view or FOV) recordings of a partial region of the body 105 in the FOV. Signals of the local coil arrangement 106 may be evaluated (e.g. converted into images, stored, or displayed) by an evaluation device (168, 115, 117, 119, 120, 121, etc.) of the MRI apparatus 101. The evaluation device may be connected to the local coil arrangement 106 (e.g., via coaxial cables or by radio 167, or the like).

In order to use a MRI apparatus 101 to examine a body 105 (e.g., an examination object or a patient) by magnetic resonance imaging, various magnetic fields accurately coordinated with one another in terms of their temporal and spatial characteristics are radiated onto the body 105. A strong magnet (e.g., a cryomagnet 107) in a measuring cabin that, in some embodiments, has an opening 103 that may be in the form of a tunnel generates a static strong main magnetic field $B_0$ that has a value of, for example, 0.2 Tesla to 3 Tesla or higher. A body 105 to be examined is laid on a patient couch 104 and moved into a region of the main magnetic field $B_0$. The main magnetic field $B_0$ is approximately homogeneous in the FOV. The nuclear spins of atomic nuclei of the body 105 are excited by magnetic radio-frequency excitation pulses B1(x, y, z, t) that are radiated in by a radio-frequency antenna (and/or, if appropriate, by a local coil arrangement). The radio-frequency antenna is shown in simplified fashion as a multi-part (e.g., 108a, 108b, 108c) body coil 108. Radio-frequency excitation pulses are generated by a pulse-generating unit 109. The pulse-generating unit 109 may be controlled by a pulse sequence control unit 110. After amplification by a radio-frequency amplifier 111, the pulses are conducted to the radio-frequency antenna 108. The radio-frequency system is shown schematically in FIG. 8. More than one pulse-generating unit 109, more than one radio-frequency amplifier 111, and a plurality of radio-frequency antennae (108a, 108b, and 108c) may be used in a magnetic resonance imaging apparatus 101.

The magnetic resonance imaging apparatus 101 has gradient coils 112x, 112y, and 112z. During a measurement, the gradient coils radiate magnetic gradient fields $B_G$(x, y, z, t) for selective slice excitation and for spatial encoding of the measurement signal. The gradient coils 112x, 112y, 112z are controlled by a gradient coil control unit 114 (and, if appropriate, by amplifiers Vx, Vy, Vz). Similar to the pulse-generating unit 109, the gradient coil control unit 114 is connected to the pulse sequence control unit 110.

Signals emitted by the excited nuclear spins (e.g., of the atomic nuclei in the examination object) are received (e.g., RF output) by the body coil 108 and/or at least one local coil arrangement 106. The signals are amplified by assigned radio-frequency preamplifiers 116 and processed further and digitized by a receiving unit 117. The recorded measurement data are digitized and stored as complex numerical values in a k-space matrix. An associated MR image may be reconstructed from the values occupying the k-space matrix by a multidimensional Fourier transformation.

For a coil that may be operated in both the transmission mode and in the reception mode (e.g., the body coil 108 or a local coil 106), the correct signal forwarding is regulated by a transmission/reception switch 118 connected upstream.

An image-processing unit 119 generates an image from the measurement data. The image is displayed to a user by an operating console 120 and/or stored in a storage unit 121. A central computer unit 122 controls the individual installation components.

In MR imaging, images with a high signal-to-noise (SNR) ratio may be recorded by local coil arrangements (e.g., coils, local coils). Local coil arrangements are antenna systems that are fitted in direct proximity on (anterior), under (posterior), at, or in the body 105. During an MR measurement, the excited nuclei induce a voltage in the individual antennae of the local coil. The induced voltage is amplified by a low-noise preamplifier (e.g. LNA, preamp) and is forwarded to the reception electronics. In order to improve the signal-to-noise ratio, even for high-resolution images, high-field installations (e.g., 1.5 T-12 T or higher) may be used. If the number of individual antennae connected to an MR reception system is greater than the number of receivers present, a switching matrix (also called RCCS) may be incorporated between reception antennae and receivers. The switching matrix routes the instantaneously active reception channels (e.g., channels that currently lie in the FOV of the magnet) to the receivers present. As a result, more coil elements may be connected than the number of receivers present. For whole body coverage, only the coils that are situated in the FOV or in the homogeneity volume of the magnet may be read.

The local coil arrangement 106 may denote an antenna system that includes, for example, one antenna element or, an array coil that includes a plurality of antenna elements (e.g., coil elements). Individual antenna elements may be embodied, for example, as loop antennae (loops), butterfly coils, flex coils, or saddle coils. A local coil arrangement may include, for example, coil elements, a preamplifier, further electronics (e.g., standing wave traps, etc.), a housing, supports, and a cable with plug for connection to the MRI installation. A receiver 168 fitted to the installation filters and digitizes a signal received from a local coil 106 (e.g., by radio, etc.), and transfers the data to a digital signal-processing device. The digital signal-processing device may derive an image or spectrum from the data obtained by a measurement and make the image or spectrum available to a user (e.g., for subsequent diagnosis by the user and/or for storage).

FIGS. 1-7 illustrate exemplary configurations in accordance with the present teachings.

In nuclear spin tomography, RF coils (also called local coils 106) in MRIs 101 may be used for receiving alternating magnetic fields. Local coils 106 are sensitive to alternating magnetic fields and may contain one or more ring-shaped (e.g., self-contained and/or continuous) loops 7 (also designated as antennae). The loops 7 may be composed of a copper conductor (also designated as a ring or frame antenna). In order to obtain a good signal-to-noise (SNR) ratio, RF coils may adapted (e.g., in terms of geometry and reception profile) for different body regions of a patient 105, and may be positioned near the body of a patient 105 during MRI imaging.

One component of a local coil 106 is the active detuning during the RF-transmission phase of the MRI 101. The active detuning is provided in order to suppress resonance during the transmission phase. The resonance may endanger the patient as a result of a local boosting of the radio-frequency radiation. Sensitive components of the local coil (e.g., a preamplifier of the local coil) are likewise protected against electrical overloading by the detuning.

As shown in FIG. 1, the active detuning may be effected by a PIN diode 3 and a quarter-wave ($\lambda/4$) line 2 in the resonant circuit of the local coil 106.

For relatively small local coils 106, the resonant circuit may be interrupted once as shown in FIG. 1.

The ratio of the diameter of the antenna 7 (e.g., self-contained, continuous, ring-shaped, elliptical, and/or butterfly-type) to the wavelength of the radio-frequency signals (e.g., RF radiation received by the patient during the MRI imaging) may determine what is large and what is small. For example, at 132 MHz, local coil antennae 7 having a diameter of up to 10 cm may be designated as small.

Figure 2:
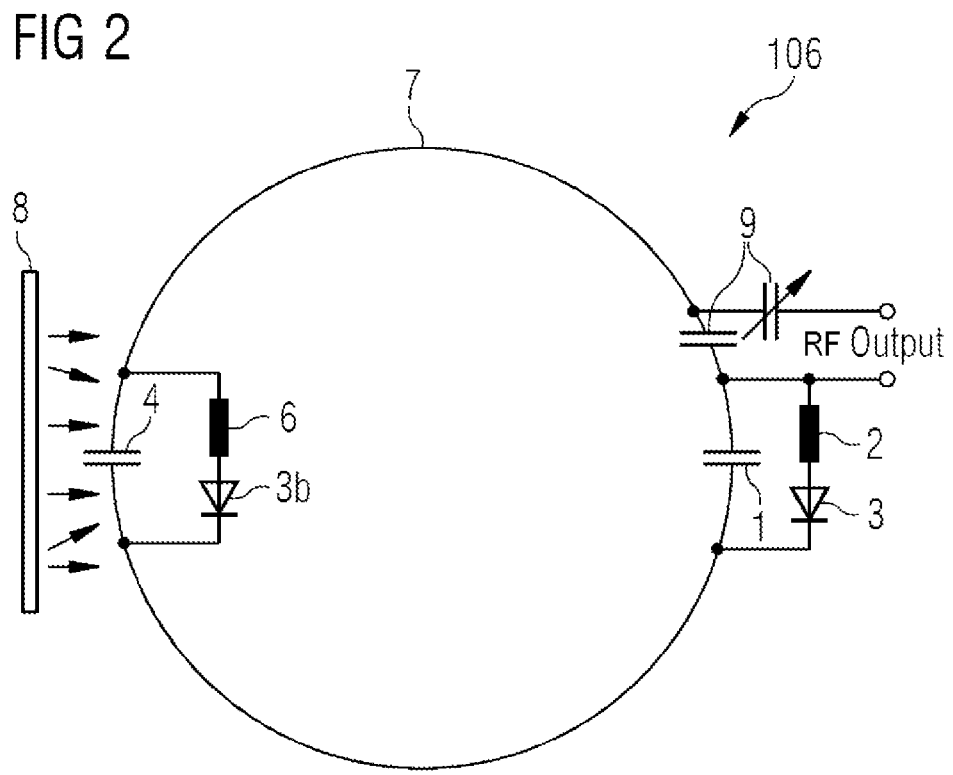
FIG. 2 shows an example of a circular loop antenna of a local coil with two detuning circuits and electrically conductive material in the vicinity of the antenna.

In the case of larger antennae 7, a second detuning device 3b may be inserted, as shown in FIG. 2. The induced voltage at the individual detuning circuit may otherwise become too high and may lead to excessively great heating or even destruction of the detuning circuit. The insertion of the second detuning circuit 3b may result in a halving of the voltage induced by the magnetic flux change.

When a second detuning circuit 3b is inserted, as shown in FIG. 2, unequal capacitive loading (e.g., as a result of electrically conducting material 8 in the vicinity of the antenna 7) may result in a non-uniform division of the voltage at the first detuning circuit 3 and the second detuning circuit 3b of the antenna 7.

Figure 5:
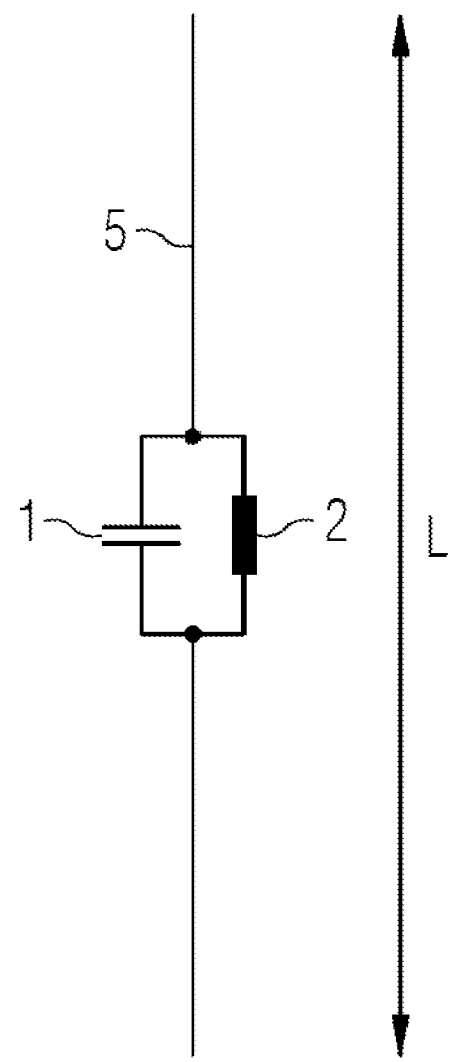
FIG. 5 shows an example of an equivalent circuit diagram of a doubly detuned coil.

In addition, as a result of a limb length L that remains too long, as shown in FIG. 5, the electric N2 dipole thus produced may still remain too close to the (MRI RF) operating frequency. The first detuning circuit 3 and the second detuning circuit 3b may be overloaded. The dipole effect may occur in the case of long coils, such as a butterfly antenna shape or a figure-eight antenna shape as shown, for example, in FIGS. 6 and 7.

Figure 3:
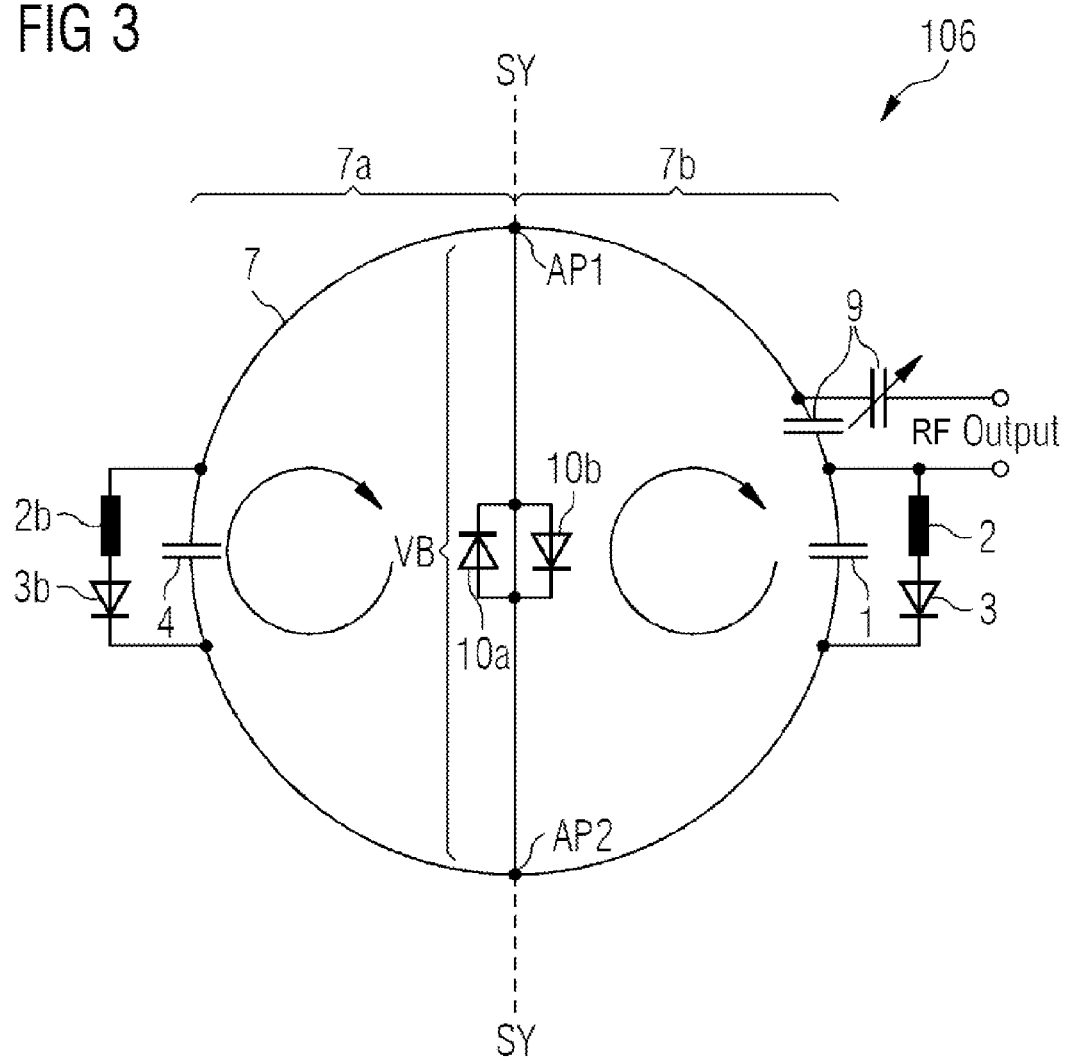
FIG. 3 shows an example of a circular loop antenna of a local coil with two detuning circuits and one additional diode in the center of the antenna.

In accordance with the present teachings, an electrical short circuit may be generated as in FIG. 3 with the aid of at least one additional switching diode (e.g., first diode 10a, second diode 10b, PIN diode 11) spatially in the center of the antenna 7 (e.g., circular, elliptical, or butterfly-type local coil).

The first diode 10a, second diode 10b, and PIN diode 11 may constrain a comparatively highly uniform voltage division by spanning two partial areas of the antenna 7 of the local coil. The first partial area and the second partial area may be identical albeit half the size as compared the configuration in FIG. 1 without diode 10/10b and 11). The magnetic flux and, therefore, the induced voltage, may be halved.

At the same time, the remaining electric dipole may be short-circuited, and electrical coupling-in via the electric field may be suppressed.

The short circuit (e.g., in PIN diode 11 or in first diode 10a and second diode 10b) is effective only in the transmission phase (e.g., when the body coil 108a, 108b, and 108c transmits RF signals into the patient).

Figure 4:
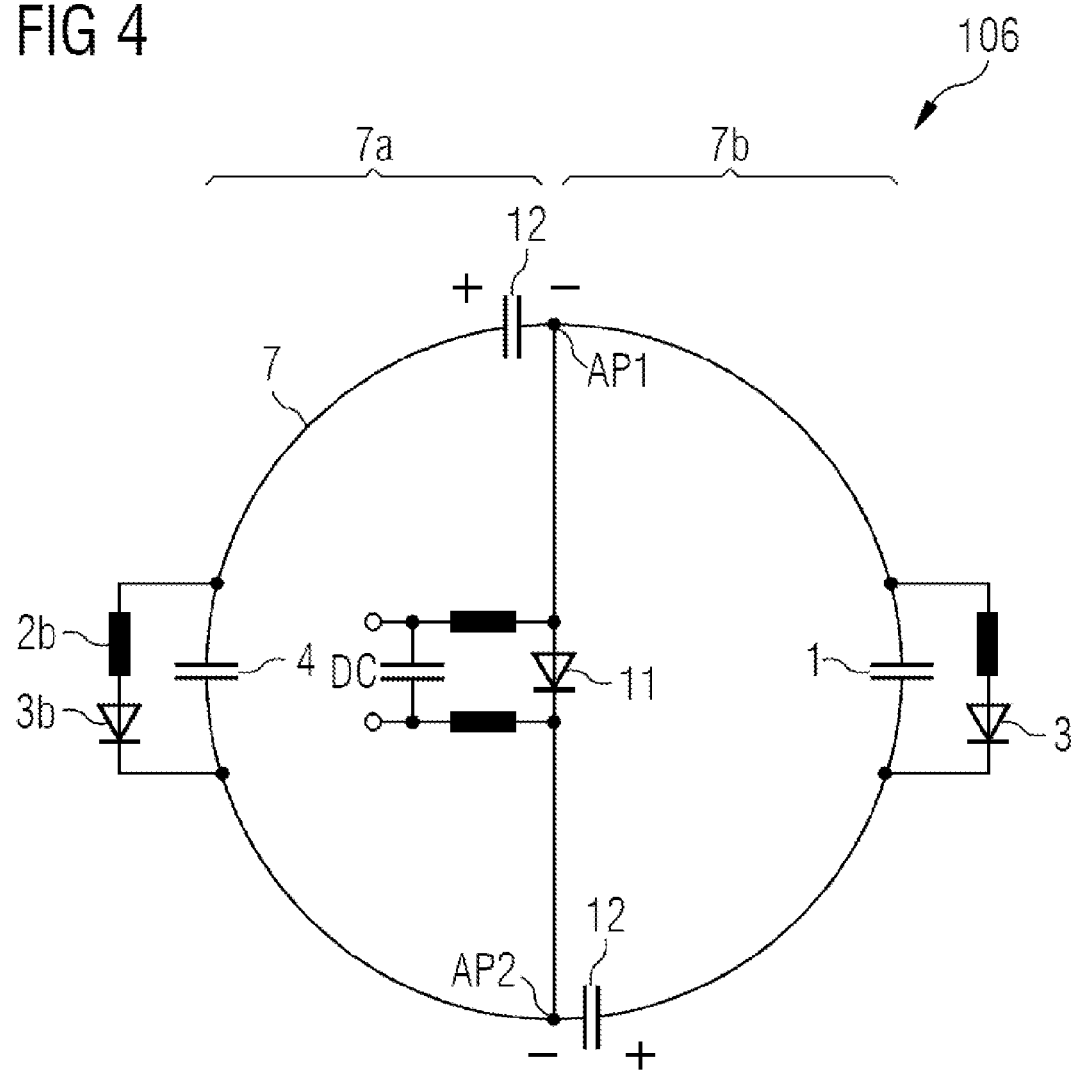
FIG. 4 shows an example of a circular loop antenna of a local coil with two detuning circuits and two additional diodes in the center of the antenna.

As shown in FIGS. 4 and 7, a diode 11 may be switched on actively (e.g., into a short circuit) with a DC current/DC voltage ("DC", "+ −") in the transmission phase (e.g., when the body coil 108a, 108b, and 108c transmits RF signals into the patient), and/or may be switched off (e.g., become non-conducting, blocking) with a negative reverse voltage ("DC" "+ −") in the reception situation (e.g., when the local coil 106 receives RF signals from the patient and outputs the signals as RF output after pre-amplification, if appropriate).

Figure 6:
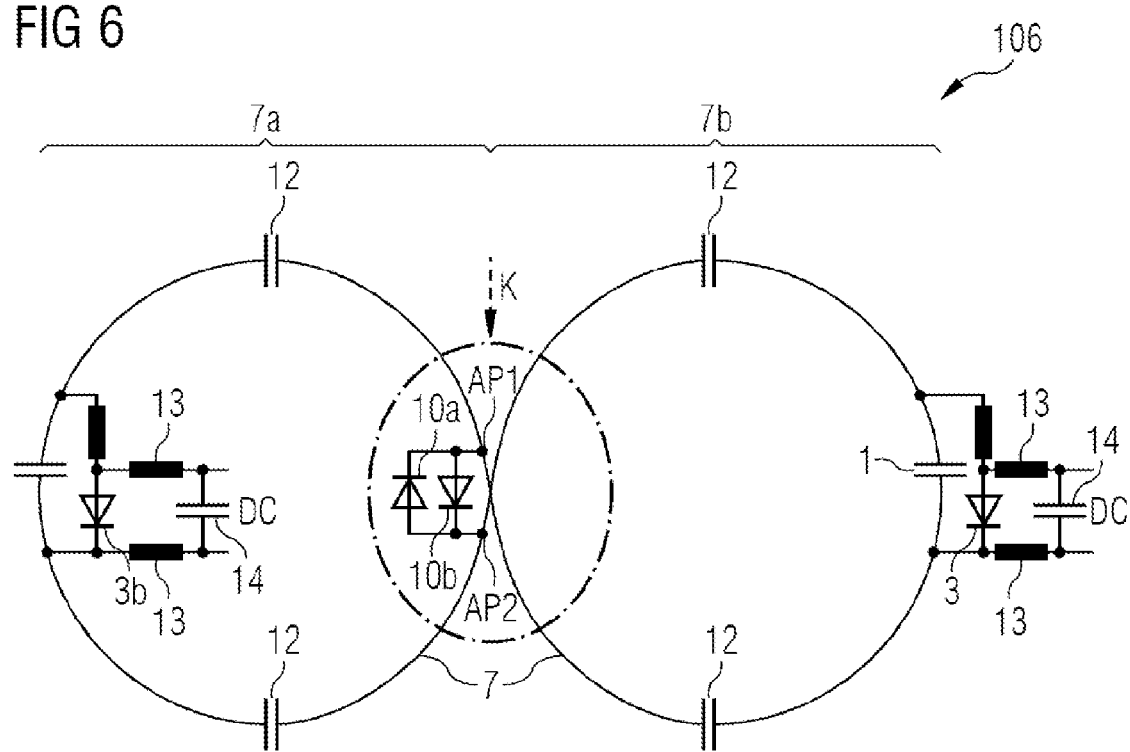
FIG. 6 shows an example of a "figure-eight" loop antenna of a local coil with two detuning circuits and one additional diode in the center of the antenna.

Alternatively, first diode 10a and second diode 10b may be connected back-to-back, as in FIGS. 3 and 6. The first diode 10a and second diode 10b switch themselves on (e.g., conducting, short circuit) and off (e.g., non-conducting, blocking) depending on voltage induced in the antenna 7 of the local coil 106 by RF signals in the transmission phase of an RF coil (e.g., 108a, 108b, 108c of the MRI).

An electrical overloading (e.g., as a result of excessive heating or voltage flashover) of a detuning circuit of a local coil may be prevented by (RF) electric field coupling-in.

A constrained balancing of the voltage drops at the detuning circuits of a local coil may be achieved. The detuning circuits may, as a result of magnetic coupling-in, be electrically identically loaded and thus heated uniformly. For uniform heating, the inductance of the detuning and the circuit quality factor may be of identical magnitude.

The drawing figures illustrate a number of exemplary solutions in accordance with the present teachings.

As shown in FIG. 3, a first diode 10a and a second diode 10b may be connected back-to-back. In the case of a passive switching, in a transmission scenario, the applied voltage of the radio-frequency signals activates the back-to-back first diode 10a and second diode 10b or, depending on the direction of the voltage, only one of the first diode 10a and second diode 10b. In a reception scenario, the voltage level may be insufficient to switch diodes.

As shown in FIG. 4 one actively switched diode 11 (e.g., a PIN diode) may be provided. In the case of active switching, in a transmission scenario, the PIN diode 11 is activated with a constant DC current (e.g., from a DC current source and/or a DC voltage source DC).

As shown in FIG. 4, in the case of additional shortening capacitors 12, the diode 11 may be connected to the capacitor connections of the additional shortening capacitors 12 with the same electrical potential ("+ –"). The losses thus introduced by the additional diode 11 may be kept small, and an induced voltage of identical magnitude may be constrained.

As shown in FIGS. 6 and 7, a butterfly design (e.g., approximating the shape of a figure-eight in cross section) may be used for the local coil 106. In the case of a butterfly design, the additional diode 11 is connected to the first partial region 7a and the second partial region 7b (e.g., spatially situated one above the other and not conductively connected) of the antenna 7 in the crossing region K of the first conduction region and the second conduction region 7b. A passive configuration (e.g., with two diodes) or an active configuration (e.g. with one diode and a DC current source) may be implemented.

The exemplary arrangements shown in the drawing figures may be combined with one another in accordance with the present teachings. For example, a circuit having two passively switching diodes and additionally a circuit having a direct-current-switched diode (or two back-to-back diodes) may be incorporated into an antenna, for example, in order to further increase reliability.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A local coil for an MRI imaging system, the local coil comprising:
   an antenna comprising a first detuning circuit and a second detuning circuit; and
   a connection connected to the antenna between a first connection point on the antenna and a second connection point on the antenna;
   wherein the connection is configured to be short-circuited by at least one diode,
   wherein the first connection point and the second connection point are situated spatially between a first partial region and a second partial region of the antenna, and
   wherein the first partial region and the second partial region of the antenna are substantially equal in size.

2. The local coil of claim 1, further comprising a connection between the first partial region and the second partial region of the antenna,
   wherein the connection between the first partial region and the second partial region of the antenna is configured for optional inhibition and activation by a single diode and a current source.

3. The local coil of claim 1, further comprising a connection between the first partial region and the second partial region of the antenna,
   wherein the connection between the first partial region and the second partial region of the antenna is configured for optional inhibition and activation by a first diode and a second diode, and
   wherein the first diode and the second diode are connected back-to-back.

4. The local coil of claim 1,
   wherein the first partial region and the second partial region form a conductor of the antenna.

5. The local coil of claim 1, wherein the first partial region and the second partial region are spatially symmetrical with respect to one another,
   wherein the at least one diode is connected to the antenna between the first connection point and the second connection point in a region between the first partial region and the second partial region.

6. The local coil of claim 1, wherein the first partial region and the second partial region are spatially symmetrical with respect to one another,
   wherein the at least one diode is connected on the antenna between the first partial region and the second partial region and between the first connection point and the second connection point, and
   wherein the first connection point and the second connection point are opposite one another in a region of an axis of mirror symmetry, on the antenna, or in the region of the axis of mirror symmetry and on the antenna.

7. The local coil of claim 1, wherein the first partial region and the second partial region are spatially symmetrical with respect to one another,
   wherein the at least one diode is connected to the antenna between the first partial region and the second partial region and between the first connection point and the second connection point,
   wherein each of the first connection point and the second connection point lies in a region of an axis of point symmetry of the antenna and in a region of overlapping crossover of the antenna, the antenna having a butterfly-type configuration.

8. The local coil of claim 1, wherein a size of the first partial area and a size of the second partial area are substantially equal in cross-section, and
   wherein the antenna is divided into the first partial area and the second partial area by an axis that runs through the first connection point and the second connection point for the at least one diode.

9. The local coil of claim 1, wherein the antenna comprises a continuous loop antenna, a self-contained loop antenna, or a continuous loop antenna and a self-contained loop antenna, and wherein the first partial region and the second partial region form the antenna.

10. The local coil of claim 1, further comprising one or more additional antennae, wherein at least one antenna of the local coil comprises a short-circuitable connection of the first connection point and the second connection point, and wherein the short-circuitable connection runs through a spatial center of the antenna.

11. The local coil of claim 1, wherein the antenna comprises a circular loop antenna, an elliptical loop antenna, a loop antenna having a figure-eight shape, or a butterfly-type loop antenna.

12. The local coil of claim 1, wherein each of the first detuning circuit and the second detuning circuit comprises a PIN diode.

13. The local coil of claim 1, wherein a short circuit is present in the connection of the first connection point and the second connection point as a result of the at least one diode only in an RF-transmission phase of the MRI imaging system.

14. The local coil of claim 1, wherein an inhibited state is present in the connection of the first connection point and the second connection point as a result of the at least one diode only in a reception phase of the local coil.

15. The local coil of claim 1, wherein each diode of the at least one diode comprises a PIN diode, a switching diode, or a PIN diode and a switching diode, and wherein the switching diode is configured for switching a short circuit or an inhibiting block.

16. The local coil of claim 1, wherein the at least one diode is connected via a connection to the antenna in a region of capacitor connections of a first shortening capacitor and a second shortening capacitor.

17. The local coil of claim 3, wherein the connection is configured for optional passive inhibition and activation by RF-induced voltage.

18. The local coil of claim 4, wherein the first partial region and the second partial region form a copper conductor of the antenna.

19. The local coil of claim 12, wherein each of the first detuning circuit and the second detuning circuit further comprises a capacitance.

20. The local coil of claim 19, wherein each of the first detuning circuit and the second detuning circuit further comprises an inductance.

* * * * *